United States Patent
Hattori

(10) Patent No.: US 7,901,562 B2
(45) Date of Patent: *Mar. 8, 2011

(54) OXYGEN SENSOR DETERIORATION DETECTION METHOD

(75) Inventor: Kazutaka Hattori, Okazaki (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 789 days.

This patent is subject to a terminal disclaimer.

(21) Appl. No.: 11/907,092

(22) Filed: Oct. 9, 2007

(65) Prior Publication Data

US 2008/0041134 A1 Feb. 21, 2008

Related U.S. Application Data

(62) Division of application No. 10/706,929, filed on Nov. 14, 2003, now Pat. No. 7,297,240.

(30) Foreign Application Priority Data

Nov. 25, 2002 (JP) ................................. 2002-341327

(51) Int. Cl.
*G01N 27/407* (2006.01)
(52) U.S. Cl. .......................... 205/785; 204/401; 204/406
(58) Field of Classification Search ................. 204/401, 204/424; 205/785; 73/23.32; 374/144; 123/697
See application file for complete search history.

(56) References Cited

U.S. PATENT DOCUMENTS

| 6,258,232 B1 | 7/2001 | Hasegawa et al. |
| 6,649,041 B2 | 11/2003 | Hashimoto et al. |

FOREIGN PATENT DOCUMENTS

| JP | A 06-347437 | 12/1994 |
| JP | A 08-278279 | 10/1996 |
| JP | A 8-313466 | 11/1996 |
| JP | A 2000-193635 | 7/2000 |
| JP | A 2001-349864 | 12/2001 |
| JP | A 2002-155796 | 5/2002 |

*Primary Examiner* — Kaj K Olsen
(74) *Attorney, Agent, or Firm* — Oliff & Berridge, PLC

(57) ABSTRACT

A deterioration detection apparatus for an oxygen sensor is able to detect an abnormality of the oxygen sensor constantly with high precision, without being affected by the temperature characteristic of the element impedance. The apparatus applies a voltage V to the oxygen sensor, and calculates an element impedance real value $Rsr=V/1$ of a sensor element based on the applied voltage and the current I caused to flow by the voltage. The apparatus calculates an element temperature estimated value Tex of the oxygen sensor from a factor that affects the temperature of the oxygen sensor. The apparatus determines whether the oxygen sensor has an abnormality on the basis of whether the relationship between the element impedance real value Rsr and the element temperature estimated value Tex can be regarded as a relationship that agrees with a normal temperature characteristic.

16 Claims, 7 Drawing Sheets

FIG.5

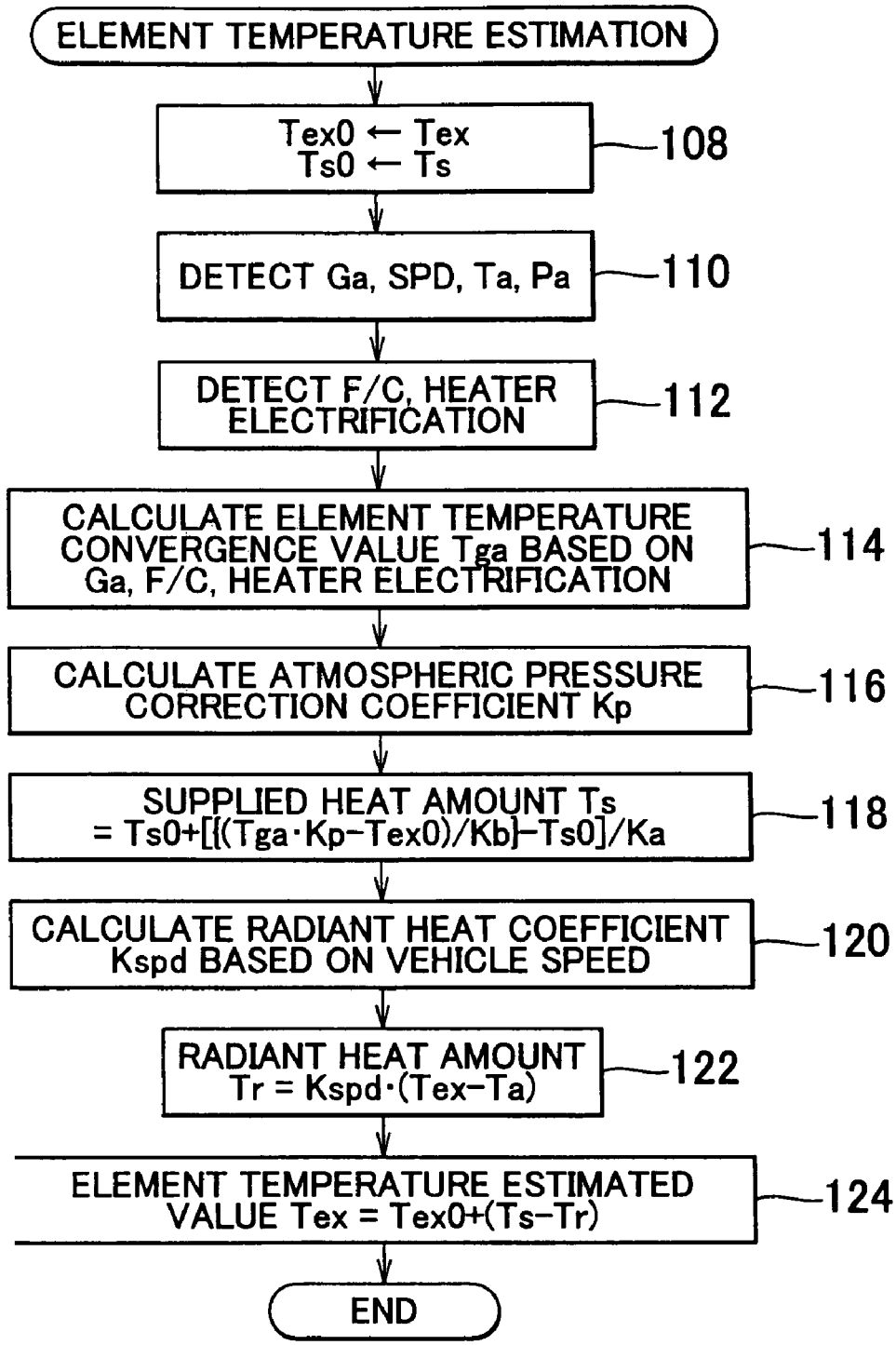

```
     ELEMENT TEMPERATURE ESTIMATION
                    │
                    ▼
         ┌──────────────────────┐
         │   Tex0 ← Tex         │──108
         │   Ts0 ← Ts           │
         └──────────────────────┘
                    │
                    ▼
         ┌──────────────────────┐
         │ DETECT Ga, SPD, Ta, Pa│──110
         └──────────────────────┘
                    │
                    ▼
         ┌──────────────────────┐
         │  DETECT F/C, HEATER  │──112
         │    ELECTRIFICATION   │
         └──────────────────────┘
                    │
                    ▼
         ┌──────────────────────────────┐
         │ CALCULATE ELEMENT TEMPERATURE│
         │ CONVERGENCE VALUE Tga BASED ON│──114
         │ Ga, F/C, HEATER ELECTRIFICATION│
         └──────────────────────────────┘
                    │
                    ▼
         ┌──────────────────────────────┐
         │ CALCULATE ATMOSPHERIC PRESSURE│──116
         │   CORRECTION COEFFICIENT Kp  │
         └──────────────────────────────┘
                    │
                    ▼
         ┌──────────────────────────────┐
         │   SUPPLIED HEAT AMOUNT Ts    │──118
         │ = Ts0+[[(Tga·Kp−Tex0)/Kb]−Ts0]/Ka│
         └──────────────────────────────┘
                    │
                    ▼
         ┌──────────────────────────────┐
         │ CALCULATE RADIANT HEAT COEFFICIENT│──120
         │    Kspd BASED ON VEHICLE SPEED │
         └──────────────────────────────┘
                    │
                    ▼
         ┌──────────────────────┐
         │  RADIANT HEAT AMOUNT │──122
         │   Tr = Kspd·(Tex−Ta) │
         └──────────────────────┘
                    │
                    ▼
         ┌──────────────────────────────┐
         │  ELEMENT TEMPERATURE ESTIMATED│──124
         │   VALUE Tex = Tex0+(Ts−Tr)   │
         └──────────────────────────────┘
                    │
                    ▼
                  ( END )
```

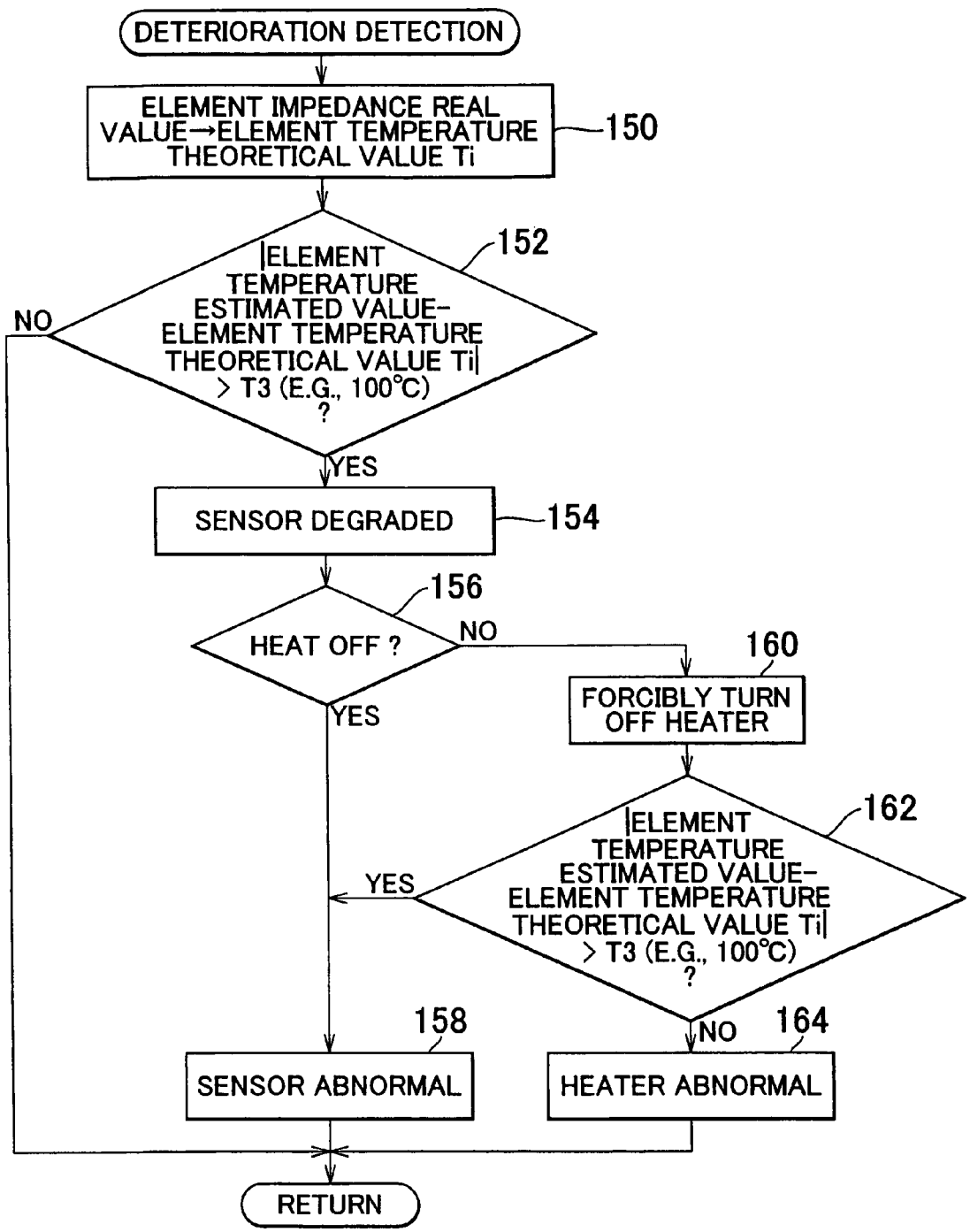

OXYGEN SENSOR DETERIORATION DETECTION METHOD

INCORPORATION BY REFERENCE

This is a Division of application Ser. No. 10/706,929 filed Nov. 14, 2003 (now published as U.S. Pat. No. 7,297,240). The disclosure of the prior application is hereby incorporated by reference herein in its entirety.

The disclosure of Japanese Patent Application No. 2002-341327 filed on Nov. 25, 2002, including the specification, drawings and abstract thereof, are incorporated herein by reference in their entirety.

BACKGROUND OF THE INVENTION

1. Field of the Invention

The invention relates to an oxygen sensor deterioration detection apparatus and method, more particularly, to a deterioration detection apparatus suitable for detecting deterioration of an oxygen sensor whose element impedance exhibits a temperature characteristic.

2. Description of the Related Art

A related-art apparatus that detects an abnormality of an oxygen sensor on the basis of an element impedance of the oxygen sensor is disclosed in Japanese Patent Application Laid-Open Publication No. 2000-198635. In this related-art detection apparatus, the oxygen sensor is disposed in an exhaust passageway of an internal combustion engine. The oxygen sensor has a heater for heating a sensor element. In a normal service environment, the temperature of the sensor element is controlled at about 700° C. via the heater and heat from exhaust gas.

In the above-described detection apparatus, a characteristic of the element impedance of the sensor element is dependent on temperature. Therefore, if the heating of the sensor element is not appropriate, the element impedance exhibits a value that is different from the value exhibited when the heating is appropriate. Utilizing this characteristic, that is, on the basis of whether the element impedance exhibits a normal value in a normal service environment, the detection apparatus detects a broken wire related to the sensor, deterioration of the heater, a broken wire related to the heater, etc.

The detection apparatus assumes that the oxygen sensor has activated, at the elapse of a predetermined time following startup of the internal combustion engine. In that condition, the apparatus determines whether the oxygen sensor has an abnormality on the basis of the element impedance, on an assumption that the oxygen sensor has been heated to about 700° C.

In reality, however, the temperature of the oxygen sensor may sometimes be apart from the vicinity of 700° C. after the elapse of a predetermined time following startup of the internal combustion engine, even if the detection system is normal. In such a case, the value of the element impedance greatly deviates from the value that is normally exhibited when the temperature of the sensor element is at or around 700° C., due to the temperature characteristic of the sensor element. As a result, a false determination of an abnormality of the oxygen sensor may be made.

SUMMARY OF THE INVENTION

As an aspect of the invention, a first deterioration detection apparatus for an oxygen sensor is provided. The detection apparatus includes first judgment value acquirer that calculates an element impedance real value from a value related to an electric power supplied to the oxygen sensor, and that acquires the calculated value as a first judgment value, a second judgment value acquirer which calculates an element temperature estimated value of the oxygen sensor from a factor that affects a temperature of the oxygen sensor, and which acquires the calculated value as a second judgment value, and an abnormality determiner that determines whether the oxygen sensor has an abnormality based on the first judgment value and the second judgment value.

A deterioration detection method realized by the first deterioration detection apparatus is also provided. The deterioration detection method includes the steps of: calculating an element impedance real value from a value related to an electric power supplied to the oxygen sensor, and acquiring the calculated value as a first judgment value; calculating an element temperature estimated value of the oxygen sensor from a factor that affects a temperature of the oxygen sensor, and acquiring the calculated value as a second judgment value; and determining whether the oxygen sensor has an abnormality based on the first judgment value and the second judgment value.

As another aspect of the invention, a second deterioration detection apparatus for an oxygen sensor is provided. This detection apparatus includes a first judgment value acquirer that calculates an element impedance real value from a value related to an electric power supplied to the oxygen sensor, and that acquires the calculated value as a first judgment value, a second judgment value acquirer which calculates an element impedance estimated value from a factor that affects a temperature of the oxygen sensor, and which acquires the calculated value as a second judgment value, and an abnormality determiner that determines whether the oxygen sensor has an abnormality based on the first judgment value and the second judgment value.

A deterioration detection method realized by the second deterioration detection apparatus is also provided. The deterioration detection method includes the steps of: calculating an element impedance real value from a value related to an electric power supplied to the oxygen sensor, and acquiring the calculated value as a first judgment value; calculating an element impedance estimated value from a factor that affects a temperature of the oxygen sensor, and acquiring the calculated value as a second judgment value; and determining whether the oxygen sensor has an abnormality based on the first judgment value and the second judgment value.

As still another aspect of the invention, a third deterioration detection apparatus for an oxygen sensor is provided. This detection apparatus includes a first judgment value acquirer that calculates an element temperature theoretical value from a value related to an electric power supplied to the oxygen sensor, and that acquires the calculated value as a first judgment value, a second judgment value acquirer which calculates an element impedance estimated value from a factor that affects a temperature of the oxygen sensor, and which acquires the calculated value as a second judgment value, and an abnormality determiner that determines whether the oxygen sensor has an abnormality based on the first judgment value and the second judgment value.

A deterioration detection method realized by the third deterioration detection apparatus is also provided. This deterioration detection method includes the steps of: calculating an element temperature theoretical value from a value related to an electric power supplied to the oxygen sensor, and acquiring the calculated value as a first judgment value; calculating an element impedance estimated value from a factor that affects a temperature of the oxygen sensor, and acquiring the calculated value as a second judgment value; and determining whether the oxygen sensor has an abnormality based on the first judgment value and the second judgment value.

As a further aspect of the invention, a fourth deterioration detection apparatus for an oxygen sensor is provided. This detection apparatus includes a first judgment value acquirer that calculates an element temperature theoretical value from a value related to an electric power supplied to the oxygen sensor, and that acquires the calculated value as a first judgment value, a second judgment value acquirer which calculates an element temperature estimated value from a factor that affects a temperature of the oxygen sensor, and which acquires the calculated value as a second judgment value, and an abnormality determiner that determines whether the oxygen sensor has an abnormality based on the first judgment value and the second judgment value.

A deterioration detection method realized by the fourth deterioration detection apparatus is also provided. This deterioration detection method includes the steps of: calculating an element temperature theoretical value from a value related to an electric power supplied to the oxygen sensor, and acquiring the calculated value as a first judgment value; calculating an element temperature estimated value from a factor that affects a temperature of the oxygen sensor, and acquiring the calculated value as a second judgment value; and determining whether the oxygen sensor has an abnormality based on the first judgment value and the second judgment value.

According to the first to fourth deterioration detection apparatuses and methods for an oxygen sensor, whether the oxygen sensor has an abnormality can be determined constantly with high precision, without being affected by the temperature characteristic of the element impedance.

BRIEF DESCRIPTION OF THE DRAWINGS

The aforementioned embodiments and other embodiments, objects, features, advantages, technical and industrial significance of the invention will be better understood by reading the following detailed description of exemplary embodiments of the invention, when considered in connection with the accompanying drawings, in which:

FIG. 5 is a flowchart illustrating a routine executed by the apparatus to estimate the element temperature of the oxygen sensor according to the embodiment of the invention;

FIG. 6 is a flowchart illustrating a routine executed by the apparatus to detect a deterioration of the oxygen sensor according to the embodiment of the invention.

DETAILED DESCRIPTION OF PREFERRED EMBODIMENTS

Figure 1:
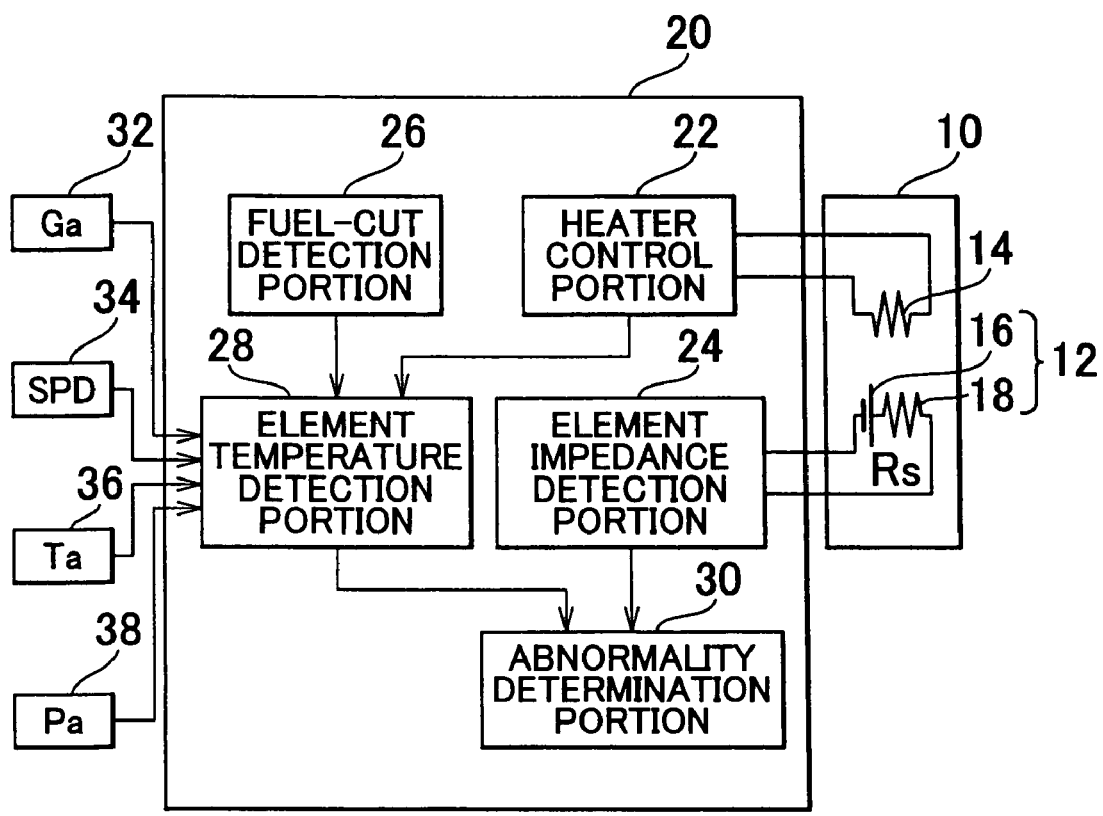
FIG. 1 is a block diagram for illustrating the construction according to an embodiment of the invention.

In the following description, the present invention will be described in more detail in terms of exemplary embodiments.

Like elements and portions of the embodiments are represented by like reference numerals in the drawings, and will not be repeatedly described below.

Embodiment

[Description of System Construction]

FIG. 1 is a block diagram for illustrating the construction of Embodiment 1 of the invention. Referring to FIG. 1, a system in accordance with this embodiment has an oxygen sensor 10. In the embodiment, the oxygen sensor 10 is disposed in an exhaust passageway of an internal combustion engine, and is used as a sensor for detecting the concentration of oxygen in exhaust gas.

The oxygen sensor 10 has a sensor element 12, and a heater 14 for heating the sensor element 12. The sensor element 12 has characteristics of generating an electromotive force corresponding to the oxygen concentration in a detection-object gas, and changing an element impedance Rs in accordance with temperature. As indicated in FIG. 1, the sensor element 12 can be equivalently represented by an electromotive force component 16 and an impedance component 18.

The oxygen sensor 10 is connected to an ECU (electronic control unit) 20. The ECU 20 is an on-vehicle computer formed by a CPU, a ROM, a RAM, electronic circuits, etc. In the embodiment, a heater control portion 22, an element impedance detection portion 24, a fuel-cut detection portion 26, an element temperature estimation portion 28 and an abnormality determination portion 30 are realized within the ECU 20 in hardware and software fashions.

The heater control portion 22 accomplishes a function of controlling the heater 14 of the oxygen sensor 10. The sensor element 12 of the oxygen sensor 10 generates an electromotive force corresponding to the oxygen concentration in a detection-object gas provided that the sensor element 12 has been heated to a predetermined temperature. Therefore, the heater control portion 22 controls the electrified and non-electrified states of the heater 14 so that the activation temperature of the sensor element 12 is maintained during operation of the oxygen sensor 10.

The element impedance detection portion 24 accomplishes a function of detecting the element impedance Rs of the sensor element 12. More specifically, the element impedance detection portion 24 supplies an appropriate electric power to the sensor element 12, and detects an element impedance Rs from a value related to the supplied power. Since the sensor element 12 is an electromotive force type sensor, it is impossible to extract a sensor output from the sensor element 12 during supply of power to the sensor element 12 (during application of voltage). Therefore, the element impedance detection portion 24 supplies power to the sensor element 12 only at a predetermined timing at which the element impedance Rs is to be detected. Then, the element impedance detection portion 24 detects the element impedance Rs in accordance with a relationship (V=Rs·I) between the applied voltage V across the sensor element 12 and the current I through the sensor element 12. Hereinafter, the element impedance Rs detected by the element impedance detection portion 24, that is, the element impedance Rs calculated from values related to the electric power supplied to the sensor element 12, will be referred to as "element impedance real value Rsr".

The element impedance detection portion 24 is provided with a first judgment value acquirer that calculates the element impedance real value Rsr, and that acquires the calculated value as a judgment value (first judgment value).

In the internal combustion engine, fuel-cut for stopping the injection of fuel is executed, for example, if the engine rotation speed is high and an accelerator pedal is released. The fuel-cut detection portion 26 accomplishes a function of detecting execution of the fuel-cut if the above-described fuel-cut is executed in the internal combustion engine. A result of detection provided by the fuel-cut detection portion 26 is supplied to the element temperature estimation portion 28.

The element temperature estimation portion 28 is supplied with information regarding the execution of fuel-cut from the fuel-cut detection portion 26 as stated above, and is also supplied with information regarding the electrification/non-electrification of the heater 14 from the heater control portion 22. The element temperature estimation portion 28 is connected to an air flow meter 32, a vehicle speed sensor 34, an intake air temperature sensor 36, and an atmospheric pressure sensor 38. Therefore, the element temperature estimation portion 28 is supplied with information regarding the amount of intake air Ga, the vehicle speed SPD, the intake air temperature Ta, and the atmospheric pressure Pa from those sensors. All the aforementioned pieces of information supplied to the element temperature estimation portion 28 concern factors that affect the temperature of the oxygen sensor 10 (sensor element 12). More specifically, the pieces of information concern major factors that affect the supplied amount of heat Ts for the oxygen sensor 10 (sensor element 12) or the amount of radiant heat Tr from the oxygen sensor 10 (sensor element 12). On the basis of the aforementioned information, the element temperature estimation portion 28 accomplishes the function of estimating the temperature of the sensor element 12. Hereinafter, the temperature of the sensor element 12 estimated by the element temperature estimation portion 28, that is, the element temperature calculated on the basis of the information regarding major factors that affect the temperature of the sensor element 12, will be referred to as "element temperature estimated value Tex".

The element temperature estimation portion 28 is provided with a second judgment value acquirer that calculates the element temperature estimated value Tex and acquires the calculated value as a judgment value (second judgment value).

The abnormality determination portion 30 determines whether the oxygen sensor 10 has an abnormality on the basis of the element impedance real value Rsr detected by the element impedance detection portion 24, and the element temperature estimated value Tex estimated by the element temperature estimation portion 28.

The abnormality determination portion 30 is provided with an abnormality determiner that determines whether the oxygen sensor 10 has an abnormality on the basis of the first judgment value acquired by the first judgment value acquirer and the second judgment value acquired by the second judgment value acquirer. The abnormality determiner is equipped with a heater electrification state detector that detects the electrified state of the heater described below, a sensor element abnormality identifier that, if it is determined that the oxygen sensor has an abnormality in a situation where the heater is not electrified, identifies the abnormality as an abnormality of the sensor element, and an electrification stopper that stops electrification of the heater if it is determined that the oxygen sensor has an abnormality in a situation where the heater is electrified. The abnormality determiner is further equipped with a first change amount detector that detects the amount of change in the first judgment value, and a second change amount detector that detects the amount of change in the second judgment value.

Figure 2:
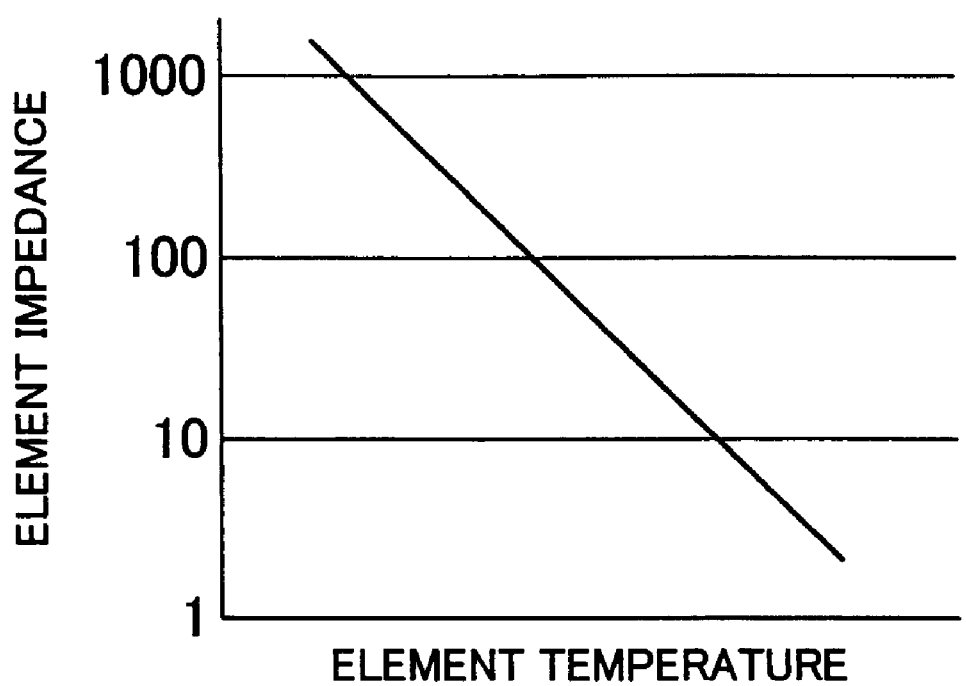
FIG. 2 is a diagram for illustrating a relationship between the element impedance and the element temperature of the sensor element.

FIG. 2 indicates a relationship between the element impedance Rs and the element temperature of the sensor element 12, that is, a temperature characteristic exhibited by the element impedance Rs of the sensor element 12. As indicated in FIG. 2, the sensor element 12 has a characteristic of decreasing the element impedance Rs exponentially with respect to increases in the element temperature.

If the oxygen sensor 10 is normal, the correlation as indicated in FIG. 2 should exist between the element impedance real value Rsr calculated from electric power-related values and the element temperature estimated value Tex estimated on the basis of a factor that affects the temperature. Therefore, the abnormality determination portion 30 determines whether the oxygen sensor 10 has an abnormality on the basis of whether a normal correlation as indicated in FIG. 2 is found between the element impedance real value Rsr and the element temperature estimated value Tex.

Figure 3:
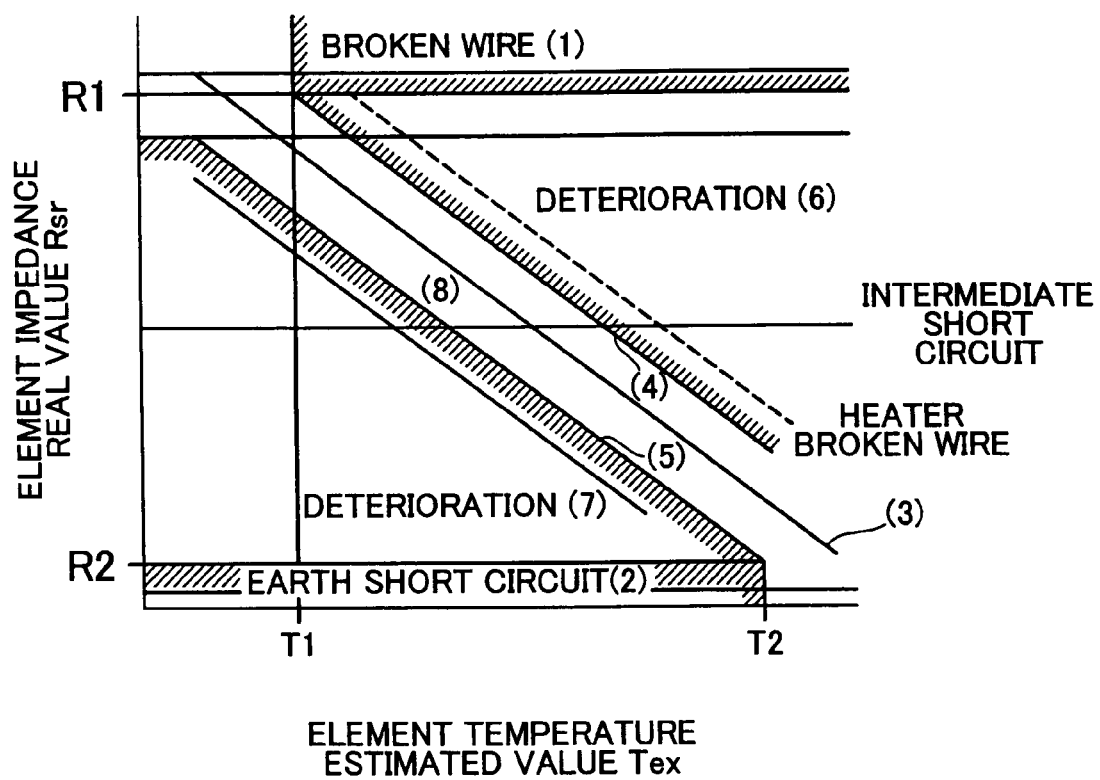
FIG. 3 is a diagram for illustrating what judgment the apparatus of the embodiment makes with reference to the relationship between the element temperature estimated value Tex and the element impedance real value Rsr.

[DESCRIPTION OF SPECIFIC CRITERIA FOR ABNORMALITY DETERMINATION] FIG. 3 is a diagram for illustrating what judgment the apparatus of the embodiment makes with reference to the relationship between the element temperature estimated value Tex and the element impedance real value Rsr. In FIG. 3, T1 and T2 on the horizontal axis indicate a lower-limit value and an upper-limit value, respectively, of a normal operation temperature range of the oxygen sensor 10. More specifically, the temperature T1 is a lower-limit temperature (e.g., 350° C.) for determining that the oxygen sensor 10 is an activated state. The temperature T2 is an upper-limit temperature (e.g., 900° C.) that the oxygen sensor 10 can reach in a normal service environment.

In FIG. 3, R1 on the vertical axis indicates an upper limit of the resistance value that will be reached only when there is a broken wire related to the sensor element 12 provided that the oxygen sensor 10 is in the activated state (provided that the temperature is at or above T1), that is, a value (e.g., 15 kΩ) that is sufficiently larger than the element impedance Rs that the sensor element 12 normally exhibits at the temperature T1. Furthermore, R2 on the vertical axis indicates a lower limit of the resistance value that will be exhibited only when the sensor element 12 has a short circuit provided that the oxygen sensor 10 is used in a normal service environment (provided that the temperature is at or below T2), that is, a value (e.g., 5Ω) that is sufficiently smaller than the element impedance Rs that the sensor element 12 normally exhibits at the temperature T2.

With the above-described settings, it can be judged that the sensor element 12 has a broken wire if the element impedance real value Rsr is greater than R1 although the element temperature estimated value Tex is higher than T1 (region (1)). If the element impedance real value Rsr is less than R2 although the element temperature estimated value Tex is lower than T2 (region (2)), it can be judged that the sensor element 12 has a short circuit. Therefore, in the embodiment, the ECU 20 judges that the sensor element 12 has a broken wire if the combination of the element temperature estimated value Tex and the element impedance real value Rsr is within the region (1). If that combination is within the region (2), the ECU 20 judges that the sensor element 12 has a short circuit.

In FIG. 3, the straight line denoted by reference numeral (3) indicates a temperature characteristic that the element temperature and the element impedance Rs normally exhibit. If the oxygen sensor 10 is normal, the combination of the element temperature estimated value Tex and the element impedance real value Rsr should be near the straight line (3) provided that the element temperature estimated value Tex is within the normal range (provided that T1<Tex<T2 holds). That is, if the combination of the element temperature estimated value Tex and the element impedance real value Rsr is far apart or remote from the straight line (3) in a situation where T1<Tex<T2 holds, it can be judged that the oxygen sensor 10 is not normal.

In FIG. 3, the straight lines denoted by reference numerals (4) and (5) are sets of points of boundary for determining that the combination of the element temperature estimated value Tex and the element impedance real value Rsr is far apart from the straight line (3). Therefore, in the embodiment, the ECU 20 determines that the sensor element 12 has deteriorated, if the combination of the element temperature estimated value Tex and the element impedance real value Rsr is in a region (6) or a region (7) shown in FIG. 3.

If the oxygen sensor 10 is normal, a correlation that agrees with the normal temperature characteristic should be found between the element temperature estimated value Tex and the element impedance real value Rsr. That is, as long as the oxygen sensor 10 is normal, a change that occurs in one of the element temperature estimated value Tex and the element impedance real value Rsr should be accompanied with an appropriate change in the other that corresponds to the aforementioned change. Therefore, it can be determined that the oxygen sensor 10 has an abnormality if a normal correlation is not found between a change $\Delta$Tex in the element temperature estimated value Tex and a change $\Delta$Rsr in the element impedance real value Rsr regardless of which region the combination of the element temperature estimated value Tex and the element impedance real value Rsr exists in (regardless of whether the combination is in a region (8) between the straight lines (4) and (5)). In the embodiment, if a phenomenon as stated above is detected, the ECU determines that the sensor element 12 has a short circuit with an intermediate impedance (hereinafter, referred to as "intermediate short circuit").

Figure 4:
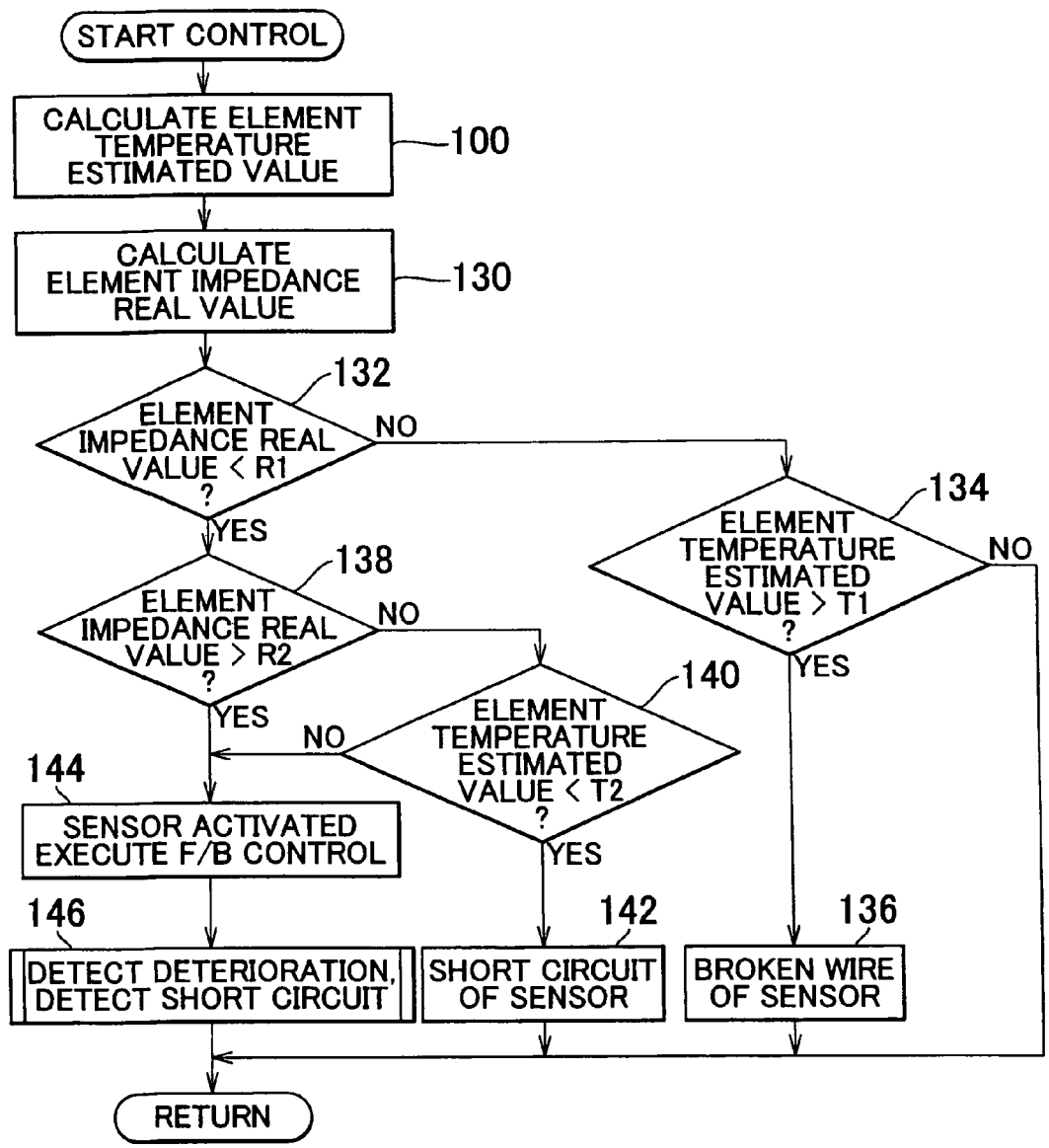
FIG. 4 is a flowchart illustrating a control routine executed by the apparatus according to the embodiment of the invention.

[DESCRIPTION OF SPECIFIC PROCESS EXECUTED FOR ABNORMALITY DETERMINATION] The contents of specific processes executed by the ECU 20 to determine whether the oxygen sensor 10 has an abnormality in accordance with the aforementioned specific criteria will be described with reference to FIGS. 4 to 7. FIG. 4 is a flowchart illustrating a control routine executed by the ECU 20 to detect a broken wire and a short circuit of the sensor element 12. In the routine illustrated in FIG. 4, an element temperature estimated value Tex of the oxygen sensor 10 is first calculated (step 100).

FIG. 5 is a flowchart illustrating the content of an element temperature estimating process executed in step 100. The element temperature estimating process is accomplished by the second judgment value acquirer.

Every time the step 100 is executed, the ECU 20 calculates an element temperature estimated value Tex following the routine illustrated in FIG. 5. In the routine illustrated in FIG. 5, the element temperature estimated value Tex and the supplied amount of heat Ts calculated in the previous execution cycle are substituted for a former element temperature estimated value Tex0 and a former supplied amount of heat Ts0, respectively (step 108). The aforementioned supplied amount of heat Ts is an amount of heat supplied to the sensor element 12. Details of the supplied amount of heat Ts and the calculation method the supplied amount of heat Ts will be described later.

In the routine illustrated in FIG. 5, the amount of intake air Ga, the vehicle speed SPD, the intake air temperature Ta and the atmospheric pressure Pa are subsequently detected via the various sensors connected to the ECU 20 (step 110).

Subsequently, information regarding the state of execution of the fuel-cut and the state of electrification of the heater 14 is detected via the fuel-cut portion detection portion 26 and the heater control portion 22 (step 112).

Next, an element temperature convergence value Tga corresponding to the present situation is calculated on the basis of the amount of intake air Ga, the state of execution of the fuel-cut and the state of electrification/non-electrification of the heater (step 114).

The element temperature convergence value Tga is greatly affected by the amount of flow and the temperature of exhaust gas. The convergence value Tga is also greatly affected by whether the heating by the heater 14 is being performed. The amount of flow of exhaust gas is, in principle, equal to the amount of intake air Ga. The temperature of exhaust gas greatly varies depending on whether the fuel-cut is being executed. Therefore, in the embodiment, the element temperature convergence value Tga is calculated on the basis of the amount of intake air Ga, the state of execution of the fuel-cut, and the state of electrification/non-electrification of the heater, as stated above. The ECU 20 stores a map that determines the element temperature convergence value Tga in relation to the aforementioned three factors. Specifically, in step 114, the element temperature convergence value Tga is determined by specifying the three factors in the map.

In the routine illustrated in FIG. 5, an atmospheric pressure correction coefficient Kp is subsequently calculated on the basis of the atmospheric pressure Pa.

The temperature of the sensor element 12 more greatly changes if the present temperature is farther apart from the element temperature convergence value Tga. That is, the amount of heat Ts supplied to the sensor element 12 has a correlation with the difference between the present element temperature and the element temperature convergence value Tga. This correlation changes with the atmospheric pressure Pa, due to the effect of air density or the like. The atmospheric pressure correction coefficient Kp is a coefficient that is determined as a value to be added to the element temperature convergence value Tga.

After the atmospheric pressure correction coefficient Kp is computed, an amount Ts of heat supplied to the sensor element 12 is computed as in the following equation (step 118).

$$Ts = Ts0 + [\{(Tga \cdot Kp - Tex0)/Kb\} - Ts0]/Ka \quad (1)$$

In equation (1), Ts0 and Tex0 are the supplied amount of heat Ts and the element temperature estimated value Tex computed in the previous execution cycle (see step 108). Furthermore, in equation (1), both Kb and Ka are annealing constants. In the right-hand side of equation (1), the term (Tga·Kp−Tex0) means the amount of heat supplied to the sensor element 12 in the present execution cycle. The term {(Tga·Kp−Tex0)/Kb} is an annealed value of the amount of heat (Tga·Kp−Tex0). Furthermore, the term [{(Tga·Kp−Tex0)/Kb}−Ts0] means the difference between the supplied amount of heat Ts0 determined in the previous execution cycle and the annealed value of the supplied amount of heat calculated in the present execution cycle. According to equation (1), the supplied amount of heat Ts in the present execution cycle is determined by reflecting, in the former supplied amount of heat Ts0, the value obtained by annealing the difference in the supplied amount of heat via Ka (by adding the Ka-annealed value to the former supplied amount of heat Ts0).

According to the processing of step 118, the heat environment existing at the time of the present execution cycle is appropriately reflected in a base, that is, the supplied amount of heat Ts0 determined in the previous execution cycle, so that the amount Ts of heat supplied to the sensor element 12 can be accurately calculated.

In the routine illustrated in FIG. 5, a radiant heat coefficient Kspd related to the vehicle speed SPD is calculated (step 120).

While the vehicle is running, the oxygen sensor 10 is cooled by vehicle-run ventilation. The radiant heat coefficient Kspd is a coefficient related to the amount of heat radiating from the oxygen sensor 10 due to the cooling by the vehicle-run ventilation. The value of the radiant heat coefficient Kspd increases with increasing vehicle speed SPD. The ECU 20 stores a map that determines a relationship between the vehicle speed SPD and the radiant heat coefficient Kspd. In step 120, the radiant heat coefficient Kspd is determined in accordance with the map.

After the radiant heat coefficient Kspd is determined, an amount of radiant heat Tr from the oxygen sensor 10 is calculated as in the following equation (step 122).

$$Tr = Kspd \cdot (Tex - Ta) \tag{2}$$

The amount of radiant heat Tr from the oxygen sensor 10 is greatly affected by the difference between the element temperature estimated value Tex and the intake air temperature Ta, as well as the vehicle speed SPD. According to equation (2), the amount of radiant heat Tr from the oxygen sensor 10 can be accurately calculated by taking the two factors into account.

Due to the above-described series of steps, the amount of heat Tr radiating from the oxygen sensor 10 and the amount Ts of heat supplied to the oxygen sensor 10 in the present execution cycle can be calculated. The ECU 20 calculates the element temperature estimated value Tex in the present execution cycle by substituting the amounts of heat Ts, Tr and the former element temperature estimated value Tex0 in the following equation (step 124).

$$Tex = Tex0 + (Ts - Tr) \tag{3}$$

With reference to the flowchart of FIG. 4 again, the control routine will be described.

After the element temperature estimated value Tex is calculated in step 100 in the routine illustrated in FIG. 4, an element impedance real value Rsr is calculated (step 130). A process of judging the element impedance real value Rsr in step 130 is accomplished by the first judgment value acquirer.

The element impedance real value Rsr is calculated on the basis of a value related to the electric power supplied to the oxygen sensor 10. More specifically, for calculation of the element impedance real value Rsr, the ECU 20 first applies a predetermined voltage V to the oxygen sensor 10. The ECU 20 then detects the current I that flows through the sensor element 12 due to application of the voltage V, and calculates the element impedance real value Rsr=V/I on the basis of the applied voltage V and the thereby-caused current I.

In the routine illustrated in FIG. 4, it is determined whether the element impedance real value Rsr is smaller than a broken wire criterion R1 (e.g., 15Ω) (step 132).

If it is determined that Rsr<R1 does not hold, that is, if it is determined that the element impedance real value Rsr is greater than or equal to the broken wire criterion R1, it is subsequently determined whether the element temperature estimated value Tex is higher than an activation criterion T1 (e.g., 350° C.) (step 134).

If it is determined that the element temperature estimated value Tex is not higher than the activation criterion T1, it can be judged that there is a possibility of the element impedance real value Rsr exceeding the broken wire criterion R1 because the oxygen sensor 10 is not activated. In this case, the determination regarding the state of the oxygen sensor 10 is suspended. After that, the present execution cycle immediately ends.

Conversely, if it is determined in step 134 that the element temperature estimated value Tex is higher than the activation criterion temperature T1, it can be judged that a falsely great value of the element impedance Rs is presented despite the activation of the oxygen sensor 10. In this case, the ECU 20 determines that the sensor element 12 has a broken wire, and ends the present execution cycle (step 136).

If it is determined in step 132 that the element impedance real value Rsr is less than the broken wire criterion R1, it is subsequently determined whether the element impedance real value Rsr is greater than a short-circuit criterion R2 (step 138).

If it is determined that Rsr>R2 does not hold, that is, if it is determined that the element impedance real value Rsr is less than or equal to the short-circuit criterion R2, it is subsequently determined whether the element temperature estimated value Tex is lower than a normal upper-limit temperature T2 (e.g., 900° C.) (step 140).

If it is determined that the element temperature estimated value Tex is not lower than the normal upper-limit temperature T2, it can be judged that there is a possibility of the element impedance real value Rsr being less than or equal to the short-circuit criterion R2 due to a high temperature of the oxygen sensor 10 above the normal temperature. In this case, the determination regarding the state of the oxygen sensor 10 is suspended. After that, a below-described process starting at step 144 is executed.

Conversely, if it is determined in step 140 that the element temperature estimated value Tex is lower than the normal upper-limit temperature T2, it can be judged that a falsely small value of the element impedance Rs of the oxygen sensor 10 is presented. In this case, the ECU 20 determines that there is a short circuit regarding the sensor element 12, and then ends the present execution cycle (step 142).

In the case where it is determined in step 138 that Rsr>R2 holds, and in the case where it is determined in step 140 that Tex<T2 does not hold, the ECU 20 determines that the oxygen sensor 10 is in the activated state. Therefore, the ECU 20 executes a known air-fuel ratio feedback control on the basis of the output of the oxygen sensor 10 (step 144).

After that, the ECU 20 executes a deterioration detection process for detecting deterioration of the oxygen sensor 10 (described below with reference to FIG. 6) and a short-circuit detection process for detecting an intermediate short circuit of the oxygen sensor 10 (described below with reference to FIG. 7), and ends the present execution cycle (step 146).

It is to be noted that the process of steps 132 to 146 is accomplished by the aforementioned abnormality determiner.

FIG. 6 shows a flowchart illustrating a deterioration detection process executed in step 146 by the ECU 20.

In the routine illustrated in FIG. 6, an element temperature theoretical value Ti is first calculated on the basis of the element impedance real value Rsr (step 150).

The element temperature and the element impedance Rs of the oxygen sensor 10 has a relationship (temperature characteristic) as indicated in FIG. 2, as described above. The ECU 20 stores a map corresponding to the relationship. In step 150, the ECU 20 calculates an element temperature theoretical value Ti corresponding to the element impedance real value Rsr in accordance with the map.

Subsequently, it is determined whether the difference |Tex−Ti| between the element temperature estimated value Tex and the element temperature theoretical value Ti is greater than a criterion T3 (e.g., 100° C.) (step 152).

The element temperature estimated value Tex is an element temperature calculated on the basis of a value that affects the temperature of the oxygen sensor 10. The element temperature theoretical value Ti is an element temperature calculated as a value corresponding to the element impedance real value Rsr, that is, an element temperature calculated on the basis of a value related to the electric power of the oxygen sensor 10. The two physical quantities, that is, the element temperature estimated value Tex and the element temperature theoretical value Ti, should coincide with each other if the oxygen sensor 10 exhibits a normal temperature characteristic. Therefore, if the difference between the two |Tex−Ti| is small, it can be judged that the temperature characteristic exhibited by the oxygen sensor 10 is normal. Conversely, if the difference |Tex−Ti| is large, it can be judged that the temperature characteristic exhibited by the oxygen sensor 10 is not normal.

The processing of step 152 is equivalent to a process of determining whether the combination of the element temperature estimated value Tex and the element impedance real value Rsr is within the region (6) or (7) indicated in FIG. 3.

In the routine illustrated in FIG. 6, if it is determined in step 152 that |Tex−Ti|>T3 does not hold, it is judged that the oxygen sensor 10 is normal. After that, the routine illustrated in FIG. 6 is promptly ended. Conversely, if it is determined that |Tex−Ti|>T3 holds, it is judged that the oxygen sensor 10 has deteriorated (step 154).

The condition examined in step 152 is fulfilled in a case where the heater 14 has an abnormality although the sensor element 12 is normal, as well as the case where the sensor element 12 has deteriorated. That is, in the embodiment, during the course of calculating the element temperature estimated value Tex, the supplied amount of heat Ts (more precisely, the element temperature convergence value Tga) differs depending on whether the heater 14 is in an electrified state or a non-electrified state (see step 114). If in an environment where the heater 14 does not perform normal function, the element temperature convergence value Tga is calculated on assumption that the heater 14 is electrified, a large error is superimposed on the element temperature estimated value Tex, so that the condition in step 152 may be satisfied. Hence, if it is determined in step 152 that the oxygen sensor 10 has deteriorated, step 152 is followed by a process for specifically determining whether the deterioration of the oxygen sensor 10 is deterioration of the sensor element 12 or deterioration of the heater 14.

Specifically, subsequently to step 154, the ECU 20 determines whether the heater 14 is the non-electrified state (step 156).

If it is determined that the heater 14 is the non-electrified state, it can be judged that the cause of the remoteness of the element temperature estimated value Tex from the element temperature theoretical value Ti is not deterioration of the heater 14. In this case, the ECU 20 identifies the content of deterioration of the oxygen sensor 10 as an abnormality of the sensor element 12 (step 158), and then ends the present execution cycle. The abnormality identification process of step 158 is accomplished by a sensor element abnormality identifier that is provided in the abnormality determiner.

Conversely, if it is determined in step 156 that the heater 14 is not in the non-electrified state, the heater 14 is forcibly switched to the non-electrified state (step 160). The dielectrification process of the step 160 is accomplished by the electrification stopper that is provided in the abnormality determiner.

The forcible setting of the heater 14 to the non-electrified state excludes deterioration of the heater 14 from the potential cause of the remoteness of the element temperature estimated value Tex from the element temperature theoretical value Ti. After step 160, the ECU 20 calculates an element temperature estimated value Tex and an element temperature theoretical value Ti again, and determines whether the difference |Tex−Ti| between the newly calculated values Tex, Ti is greater than the criterion T3 (step 162).

If it is determined in step 162 that the |Tex−Ti|>T3 holds, it can be judged that the cause of the remoteness between Tex and Ti is not abnormality of the heater 14. In this case, the ECU 20 executes the processing of step 158 to identify the content of deterioration of the oxygen sensor 10 as an abnormality of the sensor element 12, and then ends the present execution cycle.

Conversely, if it is determined in step 162 that |Tex−Ti|>T3 does not hold, it can be judged that the relationship between the element temperature estimated value Tex and the element temperature theoretical value Ti has returned to a normal relationship due to the forced diselectrification of the heater 14. In this case, the ECU 20 identifies the content of deterioration of the oxygen sensor 10 as an abnormality of the heater 14 (step 164), and then ends the present execution cycle. This abnormality identification process is accomplished by a heater electrification state detector provided in the abnormality determiner.

Figure 7:
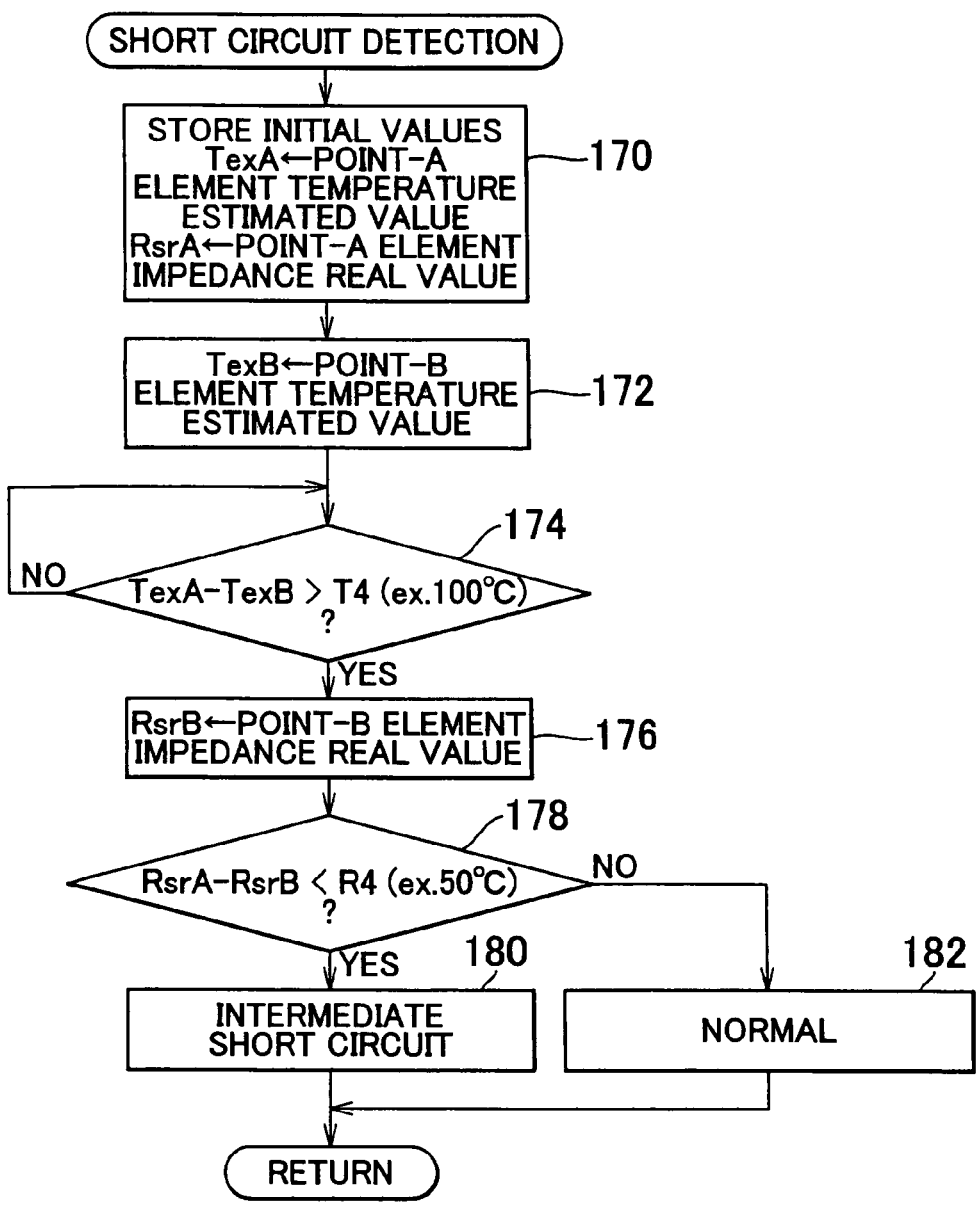
FIG. 7 is a flowchart illustrating a routine executed by the apparatus to detect an intermediate short circuit of the oxygen sensor according to the embodiment of the invention.

FIG. 7 shows a flowchart illustrating an intermediate short circuit detection process executed in step 146 by the ECU 20.

In the routine illustrated in FIG. 7, initial values of the element temperature estimated value Tex and the element impedance real value Rsr are stored (step 170).

Specifically, in step 170, the element temperature estimated value Tex and the element impedance real value Rsr determined at a time point (point A) of the first execution of this routine are stored as a point-A element temperature estimated value TexA and a point-A element impedance real value RsrA.

Subsequently, the present element temperature estimated value Tex is stored as a point-B element temperature estimated value TexB (step 172).

Subsequently, it is determined whether the difference TexA−TexB between the point-A element temperature estimated value TexA and the point-B element temperature estimated value TexB is greater than a predetermined criterion temperature T4 (e.g., 100° C.). That is, it is determined whether a change greater than the criterion temperature T4 has occurred on the element temperature estimated value Tex during the period from the detection of the point-A element temperature estimated value TexA to the present execution cycle (step 174). A process of detecting the amount of change in the element temperature estimated value Tex in step 174 is accomplished by the aforementioned second change amount detector.

The processing of step 174 is repeatedly executed until it is determined that TexA−TexB>T4 holds. When it is determined that this condition is met, the element impedance real value Rsr at that time point of determination is stored as a point-B element impedance real value RsrB (step 176).

In the routine illustrated in FIG. 7, it is subsequently determined whether the difference between the point-A element impedance real value RsrA stored in step 170 and the point-B element impedance real value Rsr stored in step 176 is less than an intermediate short-circuit criterion R4 (step 178). A process of detecting the amount of change in the element impedance real value Rsr in steps 178 is accomplished by the aforementioned first change amount detector.

The element temperature and the element impedance of the oxygen sensor 10 should have a relationship corresponding to the normal temperature characteristic. Therefore, as long as the oxygen sensor 10 is normal, a change in the element temperature estimated value Tex which is greater than the criterion temperature T4 should be accompanied by a change in the element impedance real value Rsr which corresponds to the criterion temperature T4.

The intermediate short-circuit criterion R4 used in step 178 is set at a predetermined value that is sufficiently small compared with the amount of change corresponding to the criterion temperature T4, specifically, an amount of change that should occur in the element impedance Rs when an element temperature change of T4/2 (50° C.) occurs on the oxygen sensor 10. Therefore, if it is determined that RsrA−RsfB<R4 holds, it can be judged that the amount of change in the element impedance real value Rsr is excessively small with respect to the amount of change that has occurred in the element temperature estimated value Tex.

In the routine illustrated in FIG. 7, if it is determined in step 178 that RsrA−RsfB<R4 holds, it is judged that the oxygen sensor 10 has an intermediate short circuit (step 180).

Conversely, if it is determined that RsrA−RsfB<R4 does not hold, it is judged that the oxygen sensor 10 does not have an intermediate short circuit. Hence, after it is determined that the oxygen sensor 10 is normal, the present execution cycle ends (step 182).

As is apparent from the foregoing description, it is possible to precisely determine whether there is a broken wire, a short circuit, deterioration, or an intermediate short circuit related to the oxygen sensor 10, according to the routines illustrated in FIGS. 4 to 7. Thus, the apparatus of the embodiment is able to determine whether the oxygen sensor 10 has an abnormality constantly with high precision, without being affected by the temperature characteristic of the element impedance real value Rsr, on the basis of the element impedance real value Rsr (or the element temperature theoretical value Ti) determined from a value related to the electric power supplied to the oxygen sensor 10 and the element temperature estimated value Tex calculated from a value that affects the temperature of the oxygen sensor 10.

In the embodiment described above, the determination regarding a broken wire and a short circuit and the determination regarding an intermediate short circuit (see FIGS. 4 and 7) are based on comparison between the element impedance real value Rsr and the element temperature estimated value Tex, and the determination regarding deterioration is based on comparison between the element temperature theoretical value Ti and the element temperature estimated value Tex. However, this fashion of determination is merely illustrative.

That is, in the embodiment, it is a precondition that the element impedance Rs of the oxygen sensor 10 has a temperature dependency. Therefore, since it is possible to calculate the element impedance Rs (the element impedance real value Rsr) from a value related to electric power, it is also possible to calculate an element temperature (the element temperature theoretical value Ti) from the electric power-related value. Furthermore, since it is possible to calculate the element temperature (the element temperature estimated value Tex) from a value that affects temperature, it is also possible to calculate an element impedance (hereinafter, referred to as "element impedance estimated value") on the basis of the value that affects temperature.

What is needed in order to determine whether there is a broken wire, a short circuit, deterioration or an intermediate short circuit related to the oxygen sensor 10 is that it can be determined whether there is a normal correlation between the element impedance Rs or the element temperature calculated from an electric power-related value and the element impedance Rs or the element temperature calculated from a value that affects temperature. Therefore, the aforementioned determination can be performed on the basis of any one of the following four combinations:

(a) the combination of the element impedance real value Rsr and the element temperature estimated value Tex;
(b) the combination of the element impedance real value Rsr and the element impedance estimated value;
(c) the combination of the element temperature theoretical value Ti and the element impedance estimated value; and
(d) the combination of the element temperature theoretical value Ti and the element temperature estimated value Tex.

The combination (a) corresponds to first deterioration detection apparatus and method for an oxygen sensor of the invention. The combination (b) corresponds to second deterioration detection apparatus and method for an oxygen sensor of the invention. The combination (c) corresponds to third deterioration detection apparatus and method for an oxygen sensor of the invention. The combination (d) corresponds to fourth deterioration detection apparatus and method for an oxygen sensor.

In the embodiment, the process of calculating an element temperature theoretical value Ti and acquiring the calculated value as a criterion is accomplished by the ECU 20 executing the process of step 150. Furthermore, the process of calculating an element impedance estimated value and acquiring the calculated value as a criterion is accomplished by the ECU 20 executing the process of step 100.

With the above-described construction, the invention achieves advantages as follows. According to the first oxygen sensor deterioration detection apparatus and method of the invention, whether the oxygen sensor has an abnormality can be determined constantly with high precision, without being affected by the temperature characteristic of the element impedance, on the basis of whether the element impedance real value calculated from a value related to the electric power supplied to the oxygen sensor and the element temperature estimated value calculated from a factor that affects the temperature of the oxygen sensor have a proper relationship.

According to the second oxygen sensor deterioration detection apparatus and method, whether the oxygen sensor has an abnormality can be determined constantly with high precision, without being affected by the temperature characteristic of the element impedance, on the basis of whether the element impedance real value calculated from a value related to the electric power supplied to the oxygen sensor and the element impedance estimated value calculated from a factor that affects the temperature of the oxygen sensor have a proper relationship.

According to the third oxygen sensor deterioration detection apparatus and method, whether the oxygen sensor has an abnormality can be determined constantly with high precision, without being affected by the temperature characteristic of the element impedance, on the basis of whether the element temperature theoretical value calculated from a value related to the electric power supplied to the oxygen sensor and the element impedance estimated value calculated from a factor that affects the temperature of the oxygen sensor have a proper relationship.

According to the fourth oxygen sensor deterioration detection apparatus and method, whether the oxygen sensor has an abnormality can be determined constantly with high precision, without being affected by the temperature characteristic of the element impedance, on the basis of whether the element temperature theoretical value calculated from a value related to the electric power supplied to the oxygen sensor and the element temperature estimated value calculated from a factor that affects the temperature of the oxygen sensor have a proper relationship.

Furthermore, according to deterioration detection apparatus and method in accordance with the invention, whether an oxygen sensor has an abnormality can be determined with high precision on the basis of whether the relationship between the element impedance real value and the element temperature estimated value accords with a proper temperature characteristic, or on the basis of whether the relationship between the element temperature theoretical value and the element impedance estimated value accords with a proper temperature characteristic.

Still further, according to deterioration detection apparatus and method in accordance with the invention, whether an oxygen sensor has an abnormality can be determined with high precision on the basis of whether the element impedance real value and the element impedance estimated value are substantially equal, or on the basis of whether the element temperature theoretical value and the element temperature estimated value are substantially equal.

Further, according to deterioration detection apparatus and method of the invention, if it is determined that the oxygen sensor has an abnormality in a situation where the heater is not electrified, the abnormality can be identified as an abnormality of the sensor element.

Further, according to deterioration detection apparatus and method of the invention, if it is determined that the oxygen sensor has an abnormality in a situation where the heater is electrified, the state of the heater can be excluded from the cause of the abnormality by stopping the electrification of the heater.

Further, according to deterioration detection apparatus and method of the invention, if the determination of an abnormality of the oxygen sensor is overturned by the exclusion of the state of the heater from the cause of the abnormality, it can be determined that the heater has an abnormality.

Further, according to deterioration detection apparatus and method of the invention, if the first judgment value and the second judgment value that should change in a normal correlation therebetween are not found to have the normal correlation, it can be determined that the oxygen sensor has an abnormality. The above-described techniques of determination make it possible to determine whether the oxygen sensor has an abnormality constantly with high precision without being affected by the temperature characteristic of the element impedance.

While the invention has been described with reference to exemplary embodiments thereof, it is to be understood that the invention is not limited to the exemplary embodiments or constructions. To the contrary, the invention is intended to cover various modifications and equivalent arrangements. In addition, while the various elements of the exemplary embodiments are shown in various combinations and configurations, which are exemplary, other combinations and configurations, including more, less or only a single element, are also within the spirit and scope of the invention.

What is claimed is:

1. A degradation detection method for an oxygen sensor, comprising the steps of:
   calculating an element impedance real value from a value related to an electric power supplied to the oxygen sensor, and acquiring the calculated value as a first judgment value;
   calculating an element temperature estimated value of the oxygen sensor from a factor that affects a temperature of the oxygen sensor, and acquiring the calculated value as a second judgment value; and
   determining whether the oxygen sensor has an abnormality based on the first judgment value and the second judgment value,
   wherein, in the abnormality determining step, it is determined that the oxygen sensor has an abnormality if a relationship between the first judgment value and the second judgment value does not agree with a normal temperature characteristic that is exhibited by an element impedance of the oxygen sensor,
   wherein the oxygen sensor comprises a sensor element that exhibits the temperature characteristic, and a heater for heating the sensor element,
   wherein the factor that affects the temperature of the oxygen sensor includes at least a factor related to a state of operation of the heater, and
   wherein the abnormality determining step comprises the step of detecting a state of electrification of the heater, and the step of, if it is determined that the oxygen sensor has an abnormality in a situation where the heater is not electrified, identifying the abnormality as an abnormality of the sensor element.

2. The degradation detection method according to claim 1, wherein the abnormality determining step comprises the step of stopping electrification of the heater if it is determined that the oxygen sensor has an abnormality in a situation where the heater is electrified.

3. The degradation detection method according to claim 2, wherein the abnormality determining step comprises the step of determining that the heater has an abnormality if determination of an abnormality of the oxygen sensor is overturned after the electrification of the heater is stopped in the stopping step.

4. The degradation detection method according to claim 1, wherein the abnormality determining step comprises the step of detecting an amount of change in the first judgment value, and the step of detecting an amount of change in the second judgment value, and
   wherein it is determined that the oxygen sensor has an abnormality if the amount of change in the first judgment value and the amount of change in the second judgment value do not exhibit a normal correlation.

5. A degradation detection method for an oxygen sensor, comprising the steps of:
   calculating an element impedance real value from a value related to an electric power supplied to the oxygen sensor, and acquiring the calculated value as a first judgment value;
   calculating an element impedance estimated value from a factor that affects a temperature of the oxygen sensor, and acquiring the calculated value as a second judgment value; and
   determining whether the oxygen sensor has an abnormality based on the first judgment value and the second judgment value,
   wherein in the abnormality determining step, it is determined that the oxygen sensor has an abnormality if a difference between the first judgment value and the second judgment value exceeds a predetermined criterion,
   wherein the oxygen sensor comprises a sensor element that exhibits a temperature characteristic, and a heater for heating the sensor element, wherein the factor that affects the temperature of the oxygen sensor includes at least a factor related to a state of operation of the heater, and wherein the abnormality determining step comprises the step of detecting a state of electrification of the heater, and the step of, if it is determined that the oxygen sensor has an abnormality in a situation where the heater is not electrified, identifying the abnormality as an abnormality of the sensor element.

6. The degradation detection method according to claim 5, wherein the abnormality determining step comprises the step of stopping electrification of the heater if it is determined that the oxygen sensor has an abnormality in a situation where the heater is electrified.

7. The degradation detection method according to claim 6, wherein the abnormality determining step comprises the step of determining that the heater has an abnormality if determination of an abnormality of the oxygen sensor is overturned after the electrification of the heater is stopped in the stopping step.

8. The degradation detection method according to claim 5,
wherein the abnormality determining step comprises the step of detecting an amount of change in the first judgment value, and the step of detecting an amount of change in the second judgment value, and
wherein it is determined that the oxygen sensor has an abnormality if the amount of change in the first judgment value and the amount of change in the second judgment value do not exhibit a normal correlation.

9. A degradation detection method for an oxygen sensor, comprising the steps of:
calculating an element temperature theoretical value from a value related to an electric power supplied to the oxygen sensor, and acquiring the calculated value as a first judgment value;
calculating an element impedance estimated value from a factor that affects a temperature of the oxygen sensor, and acquiring the calculated value as a second judgment value; and
determining whether the oxygen sensor has an abnormality based on the first judgment value and the second judgment value,
wherein in the abnormality determining step, it is determined that the oxygen sensor has an abnormality if a relationship between the first judgment value and the second judgment value does not agree with a normal temperature characteristic that is exhibited by an element impedance of the oxygen sensor,
wherein the oxygen sensor comprises a sensor element that exhibits the temperature characteristic, and a heater for heating the sensor element,
wherein the factor that affects the temperature of the oxygen sensor includes at least a factor related to a state of operation of the heater, and
wherein the abnormality determining step comprises the step of detecting a state of electrification of the heater, and the step of, if it is determined that the oxygen sensor has an abnormality in a situation where the heater is not electrified, identifying the abnormality as an abnormality of the sensor element.

10. The degradation detection method according to claim 9, wherein the abnormality determining step comprises the step of stopping electrification of the heater if it is determined that the oxygen sensor has an abnormality in a situation where the heater is electrified.

11. The degradation detection method according to claim 10, wherein the abnormality determining step comprises the step of determining that the heater has an abnormality if determination of an abnormality of the oxygen sensor is overturned after the electrification of the heater is stopped in the stopping step.

12. The degradation detection method according to claim 9,
wherein the abnormality determining step comprises the step of detecting an amount of change in the first judgment value, and the step of detecting an amount of change in the second judgment value, and
wherein it is determined that the oxygen sensor has an abnormality if the amount of change in the first judgment value and the amount of change in the second judgment value do not exhibit a normal correlation.

13. A degradation detection method for an oxygen sensor, comprising the steps of:
calculating an element temperature theoretical value from a value related to an electric power supplied to the oxygen sensor, and acquiring the calculated value as a first judgment value;
calculating an element temperature estimated value from a factor that affects a temperature of the oxygen sensor, and acquiring the calculated value as a second judgment value; and
determining whether the oxygen sensor has an abnormality based on the first judgment value and the second judgment value,
wherein in the abnormality determining step, it is determined that the oxygen sensor has an abnormality if a difference between the first judgment value and the second judgment value exceeds a predetermined criterion,
wherein the oxygen sensor comprises a sensor element that exhibits a temperature characteristic, and a heater for heating the sensor element,
wherein the factor that affects the temperature of the oxygen sensor includes at least a factor related to a state of operation of the heater, and
wherein the abnormality determining step comprises the step of detecting a state of electrification of the heater, and the step of, if it is determined that the oxygen sensor has an abnormality in a situation where the heater is not electrified, identifying the abnormality as an abnormality of the sensor element.

14. The degradation detection method according to claim 13, wherein the abnormality determining step comprises the step of stopping electrification of the heater if it is determined that the oxygen sensor has an abnormality in a situation where the heater is electrified.

15. The degradation detection method according to claim 14, wherein the abnormality determining step comprises the step of determining that the heater has an abnormality if determination of an abnormality of the oxygen sensor is overturned after the electrification of the heater is stopped in the stopping step.

16. The degradation detection method according to claim 13,
wherein the abnormality determining step comprises the step of detecting an amount of change in the first judgment value, and the step of detecting an amount of change in the second judgment value, and
wherein it is determined that the oxygen sensor has an abnormality if the amount of change in the first judgment value and the amount of change in the second judgment value do not exhibit a normal correlation.

* * * * *